United States Patent
Nezhat

[11] Patent Number: 6,123,701
[45] Date of Patent: Sep. 26, 2000

[54] METHODS AND SYSTEMS FOR ORGAN RESECTION

[75] Inventor: Camran Nezhat, Woodside, Calif.

[73] Assignee: Perfect Surgical Techniques, Inc., Palo Alto, Calif.

[21] Appl. No.: 09/169,019

[22] Filed: Oct. 8, 1998

Related U.S. Application Data

[63] Continuation-in-part of application No. 08/948,282, Oct. 9, 1997.

[51] Int. Cl.$^7$ .................................................. A61B 18/04
[52] U.S. Cl. ................................ 606/33; 606/39; 606/50; 600/564
[58] Field of Search ........................... 606/33–34, 41–42, 606/45–52, 76

[56] References Cited

U.S. PATENT DOCUMENTS

| | | |
|---|---|---|
| 3,920,021 | 11/1975 | Hiltebrandt . |
| 4,041,952 | 8/1977 | Morrison, Jr. et al. . |
| 4,671,274 | 6/1987 | Sorochenko . |
| 5,037,379 | 8/1991 | Clayman et al. ........................... 600/37 |
| 5,151,102 | 9/1992 | Kamiyama et al. . |
| 5,207,691 | 5/1993 | Nardella . |
| 5,217,030 | 6/1993 | Yoon . |
| 5,267,998 | 12/1993 | Hagen . |
| 5,269,780 | 12/1993 | Roos . |
| 5,269,782 | 12/1993 | Sutter . |
| 5,281,216 | 1/1994 | Klicek . |
| 5,282,799 | 2/1994 | Rydell . |
| 5,290,287 | 3/1994 | Boebel et al. . |
| 5,295,990 | 3/1994 | Levin . |
| 5,300,087 | 4/1994 | Knoepfler . |
| 5,324,289 | 6/1994 | Eggers . |
| 5,330,471 | 7/1994 | Eggers ....................................... 606/48 |
| 5,336,229 | 8/1994 | Noda . |
| 5,336,237 | 8/1994 | Chin et al. ............................... 606/167 |
| 5,342,381 | 8/1994 | Tidemand . |
| 5,352,223 | 10/1994 | McBrayer et al. . |
| 5,352,235 | 10/1994 | Koros et al. . |
| 5,356,408 | 10/1994 | Rydell . |
| 5,391,166 | 2/1995 | Eggers . |
| 5,395,369 | 3/1995 | McBrayer et al. . |
| 5,396,900 | 3/1995 | Slater et al. . |
| 5,417,687 | 5/1995 | Nardella et al. . |
| 5,423,814 | 6/1995 | Zhu et al. . |
| 5,443,463 | 8/1995 | Stern et al. . |
| 5,445,638 | 8/1995 | Rydell et al. . |
| 5,456,684 | 10/1995 | Schmidt et al. . |
| 5,458,598 | 10/1995 | Feinberg et al. . |
| 5,462,546 | 10/1995 | Rydell . |
| 5,482,054 | 1/1996 | Slater et al. . |
| 5,484,435 | 1/1996 | Fleenor et al. . |
| 5,484,436 | 1/1996 | Eggers et al. . |
| 5,496,312 | 3/1996 | Klicek . |
| 5,496,317 | 3/1996 | Goble et al. . |
| 5,514,134 | 5/1996 | Rydell et al. . |
| 5,531,744 | 7/1996 | Nardella et al. . |
| 5,540,684 | 7/1996 | Hassler, Jr. . |
| 5,540,685 | 7/1996 | Parins et al. . |
| 5,542,945 | 8/1996 | Fritzsch . |
| 5,549,606 | 8/1996 | McBrayer et al. . |
| 5,558,100 | 9/1996 | Cox . |
| 5,558,671 | 9/1996 | Yates . |
| 5,569,243 | 10/1996 | Kortenbach et al. . |
| 5,573,535 | 11/1996 | Viklund . |
| 5,578,052 | 11/1996 | Koros et al. . |
| 5,599,350 | 2/1997 | Schulze et al. . |
| 5,603,711 | 2/1997 | Parins et al. . |
| 5,611,803 | 3/1997 | Heaven et al. ............................ 606/47 |
| 5,624,452 | 4/1997 | Yates . |

(List continued on next page.)

*Primary Examiner*—Cary O'Connor
*Assistant Examiner*—Michael Astorino
*Attorney, Agent, or Firm*—Townsend and Townsend and Crew LLP

[57] ABSTRACT

Methods and systems are provided for necrosing and resecting tissue. A pair of electrodes are placed on opposed tissue surfaces, and radio frequency power is applied through the electrodes to necrose a tissue mass therebetween. After necrosis has been effected, the tissue may be resected along a plane within the necrosed region with minimum or no bleeding. The tissue mass may then be removed.

28 Claims, 14 Drawing Sheets

U.S. PATENT DOCUMENTS

| | | |
|---|---|---|
| 5,637,110 | 6/1997 | Pennybacker et al. . |
| 5,637,111 | 6/1997 | Sutcu et al. . |
| 5,653,692 | 8/1997 | Masterson et al. ............... 604/113 |
| 5,658,281 | 8/1997 | Heard . |
| 5,665,085 | 9/1997 | Nardella . |
| 5,665,100 | 9/1997 | Yoon . |
| 5,667,526 | 9/1997 | Levin . |
| 5,669,907 | 9/1997 | Platt, Jr. et al. . |
| 5,674,184 | 10/1997 | Hassler, Jr. . |
| 5,674,220 | 10/1997 | Fox et al. . |
| 5,681,282 | 10/1997 | Eggers et al. . |
| 5,683,385 | 11/1997 | Kortenbach et al. . |
| 5,683,388 | 11/1997 | Slater . |
| 5,688,270 | 11/1997 | Yates et al. . |
| 5,693,051 | 12/1997 | Schulze et al. . |
| 5,697,949 | 12/1997 | Giurtino et al. . |
| 5,700,261 | 12/1997 | Brinkerhoff . |
| 5,702,390 | 12/1997 | Austin et al. . |
| 5,707,369 | 1/1998 | Vaitekunas et al. . |
| 5,709,680 | 1/1998 | Yates et al. . |
| 5,713,896 | 2/1998 | Nardella . |
| 5,718,703 | 2/1998 | Chin . |
| 5,733,283 | 3/1998 | Malis et al. . |
| 5,735,289 | 4/1998 | Pfeffer et al. ............... 128/751 |
| 5,735,848 | 4/1998 | Yates et al. . |
| 5,735,849 | 4/1998 | Baden et al. . |
| 5,741,285 | 4/1998 | McBrayer et al. . |
| 5,743,906 | 4/1998 | Parins et al. ............... 606/51 |
| 5,755,717 | 5/1998 | Yates et al. . |

METHODS AND SYSTEMS FOR ORGAN RESECTION

The present application is a continuation-in-part of application Ser. No. 08/948,282, filed on Oct. 9, 1997, the full disclosure of which is incorporated herein by reference.

BACKGROUND OF THE INVENTION

1. Field of the Invention

The present invention relates generally to tissue resection, and more particularly to methods and systems for resecting tissue after tissue necrosis.

Tissue and organ removal are required in a number of surgical procedures for a number of purposes. A major concern in all tissue removal procedures is hemostasis, i.e. cessation of bleeding. All blood vessels supplying an organ or a tissue segment to be removed have to be sealed, either by suturing or cauterization, to inhibit bleeding when the tissue is removed. For example, when the uterus is removed in a hysterectomy, bleeding must be inhibited in the cervical neck which is resected as well as along the vessels which supply blood to the uterus along its sides. Similarly, blood vessels within the liver must be individually sealed when a portion of the liver is resected in connection with removal of a tumor or for other purposes. The liver is a highly vascularized organ and sealing of the blood vessels is quite time consuming. Achieving hemostasis is necessary in both open surgical procedures and in minimally invasive surgical procedures. In the latter case, however, because of the limited access through cannula and other small passages, sealing of blood vessels can be even more time consuming and problematic.

Achieving hemostasis is particularly important in laparoscopic and other limited access procedures where the organ or other tissue must be "morcellated" prior to removal. Most organs are too large to be removed intact through a cannula or other limited access passage, thus requiring that the tissue be morcellated, e.g. cut, ground, or otherwise broken into smaller pieces, prior to removal. It will be appreciated that morcellation of vascularized tissue can be very problematic.

For these reasons, it would be desirable to provide improved methods, systems, and apparatus, for achieving hemostasis in connection with organ and tissue removal procedures. In particular, it would be desirable to provide methods and systems which permit a surgeon to achieve hemostasis in a time-efficient manner, using readily available surgical equipment (e.g. radio frequency power supplies as discussed below), while reducing risk and trauma to the patient. It would be further desirable if the methods and systems are applicable to a wide variety of tissue removal procedures, including at least hysterectomies, liver tissue resection, cholecystectomies, prostate removal, lung resection, and the like. It would be still further desirable if the methods could provide for complete or substantially complete coagulation and hemostasis of an entire volume of tissue to be removed in order to facilitate subsequent morcellation. The ability to morcelate tissue while minimizing bleeding will be of substantial benefit to the performance of laparoscopic and other minimally invasive procedures. At least some of these objective will be met by the invention described and claimed hereinafter.

2. Description of the Background Art

The use of radio frequency (RF) energy to necrose body organs or portions thereof is known. U.S. Pat. No. 4,979,948 describes a balloon electrode which is inflated in the interior of a uterus and used to apply RF energy to necrose the endothelial lining of the uterus. U.S. Pat. No. 3,845,771 describes a glove having flexible electrodes on the thumb and middle finger. The glove is intended for conducting RF current to conventional forceps, scalpels, etc. U.S. Pat. No. 4,972,846 describes electrode patch pairs useful as defibrillator leads which are engaged directly on the epicardium. U.S. Pat. Nos. 5,178,618 and 5,078,736 describe stents which can be energized to apply RF energy on the interior of a body lumen. Lorentzen et al. (1996) *Min. Ivas. Ther. Allied Technol.* 5:511–516 describes a loop electrode that can be rotated within tissue to excuse a tissue volume.

SUMMARY OF THE INVENTION

The present invention provides methods, systems, and apparatus which facilitate tissue resection and removal from patients undergoing a wide variety of procedures. The procedures may involve removal of an entire organ, e.g. hysterectomies, cholecystectomies, prostate removal, lung resection, and the like. Alternatively, the methods may involve removal of a portion of an organ or other tissue, such as tumor removal, often from highly vascularized organs, such as the liver, lung, or the like. The methods generally involve two steps, where the tissue is first necrosed in whole or in part using radio frequency energy. In particular, the necrosis is effected at least along a desired resection plane within the tissue. The tissue is then resected along said plane(s). Advantageously, it has been found that resection within the necrosed tissue substantially minimizes, and in some cases eliminates, the bleeding caused by the tissue resection. Preferably, the tissue necrosis will be effected over a target volume of tissue, typically an entire organ or a portion thereof, e.g. the uterus, the lobe of a liver, a lung section, the prostate, or the like. By effecting substantially complete necrosis of a target tissue volume, the bleeding capacity of that tissue is reduced or eliminated, thus facilitating subsequent morcellization and tissue removal. Thus, organ and tissue removal is greatly facilitated with a substantial reduction in bleeding and the time needed for the surgical procedure.

In a first specific aspect, methods according to the present invention comprise engaging at least a first electrode structure and a second electrode structure against spaced-apart surfaces of a tissue mass, typically against opposed surfaces of the tissue mass. The first and second electrode structures may have generally similar geometries in order to contact tissue in a symmetric fashion. Alternatively, the electrode structures may have dissimilar geometries, e.g. one of the electrode structures may be configured as a probe for insertion into a natural body orifice with the other electrode structure being configured for engagement against an exterior tissue surface spaced-apart from said orifice. In some instances, more than two electrode structures may be employed, but at least two electrode structures (or separate regions of a single structure) will be energized with opposite polarity to provide for application of the radio frequency energy to the tissue. In some other instances, the electrode structures may be different regions formed as part of a single support structure, e.g. a single elastic tube or shell which may be placed over an organ or other tissue mass and which has two or more electrode surfaces formed thereon. The different electrode surfaces will, of course, be isolated from each other when they are intended to apply high frequency energy of opposite polarities. In still other instances, a single electrode structure may have two or more electrically conductive or active regions, where the electrically conductive regions may be energized with the same or an opposite polarity. In other instances, electrode structures may be provided with tissue-penetrating elements to enhance electrode-tissue contact and increase the total available area of the electrically active region(s) on the electrode structure to deliver high frequency energy to the tissue. The use of such tissue-penetrating elements may be in addition to or in place of the use of conformable or rigid "surface" electrodes. In all instances, the electrode structures, or electrically active regions thereof, will be configured to engage a substantially continuous segment or portion of the tissue surface having a minimum area as set forth below. When tissue-penetrating elements are used, they will typically be dispersed in a general uniform matter over the electrically active area of the electrode structure.

High frequency (usually radio frequency) power is applied to the tissue mass through the electrically active regions(s) of the electrode structures, and the power is applied for a time and in an amount sufficient to necrose tissue between said electrodes, preferably at least along a desired resection plane. Often, a volume of the necrosed tissue will be resected by morcellating, e.g. grinding, comminuting, cutting into small pieces, or the like. Such morcellation is greatly facilitated by necrosis of the target tissue volume. By "necrosed," it is meant that the cells of the tissue have been killed and that bleeding of the tissue, upon subsequent resection, has been substantially inhibited. The tissue will usually be resected along a plane within the necrosed tissue mass, with minimal bleeding as described above.

The electrically active regions of the electrode structures will have an area of at least 1 $cm^2$, more usually at least 2 $cm^2$, often having areas of 5 $cm^2$ or larger, more often having areas of 10 $cm^2$ or larger, still more often having areas of 50 $cm^2$ or larger. The electrodes may have a wide variety of characteristics, may generally be rigid, flexible, elastic, malleable, conformable, or the like. Preferably, the electrodes will be flexible to facilitate engagement of the electrode against a tissue surface. In at least some instances, it will be desirable to provide flexible, elastic electrodes which may be conformed about the outer periphery of a tissue or organ surface, where the elastic nature of the electrode assures firm engagement and electrode contact. In other instances, however, the electrodes may be specifically configured to have a desired geometry for engaging a particular tissue surface. For example, as described in more detail below, a pair of opposed half-ring electrodes may be configured to engage opposed surfaces of the cervical neck of the uterus. Such half-ring electrodes may be flexible but nondistensible, and could even be rigid so long as they were sized properly to engage the cervical neck tightly.

The tissue resection methods of the present invention may be performed as part of open surgical procedures or as part of minimally invasive surgical procedures. In the latter case, the electrodes will typically be introduced through a percutaneous port, e.g. a cannula introduced through the patient's skin in a conventional manner. Such minimally invasive procedures will frequently be performed as part of laparoscopic, thoracoscopic, arthroscopic, or other procedures where the operating field is viewed on a video screen through an appropriate scope. In the case of minimally invasive procedures, the electrodes will typically be introduced in a collapsed configuration and expanded within the operating field prior to contact against the target tissue surface.

The high frequency energy applied to the organ or tissue will generally be provided at radio frequency, typically in the range from 100 kHz to 10 MHz, usually from 200 kHz to 750 kHz. The power levels will depend on the surface area and volume of tissue being treated, but will generally fall within the range from 10 W to 500 W, usually from 25 W to 200 W, more usually from 50 W to 100 W. Power will usually be applied at a level of from 1 $W/cm^2$ to 10 $W/cm^2$, more usually from 1 $W/cm^2$ to 5 $W/cm^2$. The power will be applied for a time sufficient to raise the tissue temperature in the tissue mass being treated to above a threshold level required for necrosis, usually being above at least 60° C., frequently being above 70° C., and often above 80° C., or higher. The application of energy should be limited, however, so that adjacent tissue is not significantly heated or otherwise damaged. The use of opposed, bipolar electrodes is particularly advantageous in this regard since it concentrates the energy flux between the electrodes and limits the effect on adjacent tissue which are not confined within the opposed electrodes. The resulting necrosed tissue may comprise substantially the entire organ being treated, or in other cases may comprise a more narrow region, e.g. a planar, disk-like region achieved by applying opposed half-ring electrodes.

In another aspect, the present invention comprises systems including at least a first electrode, a second electrode, and a power supply connectable to the first and second electrodes for applying bipolar, high frequency power therebetween. The electrodes may be configured generally as described above, and will usually be carried by an electrosurgical probe to facilitate deployment. The probe may have a wide variety of configurations, but will usually comprise at least a shaft and a handle for manipulating the shaft. The first and second electrodes will be mounted at a distal end of the shaft and will usually be manipulable from the proximal end of the shaft so that they may be opened and closed relative to each other to engage and capture an organ or other tissue mass therebetween. The electrodes may have any of the properties described above, and may in particular comprise metallic or metallized mesh which can elastically engage and conform to tissue surfaces. In the case of electrosurgical probes intended for minimally invasive procedures, the shaft will typically have a diameter below 15 mm, usually below 12 mm, often below 10 mm, and sometimes below 5 mm, in order to conform to conventional percutaneous cannulas. Usually, the electrodes will be retractable within the shaft of such probes, and a mechanism will be provided for advancing and retracting the electrodes from the distal tip thereof. The electrodes will thus need to be expansible from a retracted configuration (when retracted within the probe shaft) to an expanded configuration, when advanced from said shaft. Such expansibility may be provided by spring mechanisms, actively expansible jaws, or other conventional design features. The electrosurgical probes may be used in a conventional bipolar manner, i.e. where each electrode is powered at an opposite polarity. Alternatively, the first and second (and optionally additional) electrode surfaces may be powered at the same polarity with another electrode or electrodes utilized for completing the high frequency circuit. Typically, the other electrode(s) will be in the form of one or more probes which may be inserted into a natural body orifice or lumen or may be introduced into an organ or other tissue mass. The probe(s) may conform to a natural lumen and/or saline or other electrically conductive fluid may be introduced into the lumen to help establish the conductive path.

In a specific embodiment, an electrosurgical device may comprise a single conformable structure, such as an elastically or non-elastically expansible tubular member, e.g. an expansible tubular braid mesh. The electrodes are formed on two or more locations over the conformable support structure and are usually isolated from each other, e.g. either by applying insulation or by relying on the inherently non-conductive nature of the conformable support structure.

DESCRIPTION OF THE SPECIFIC EMBODIMENTS

Figure 1A:
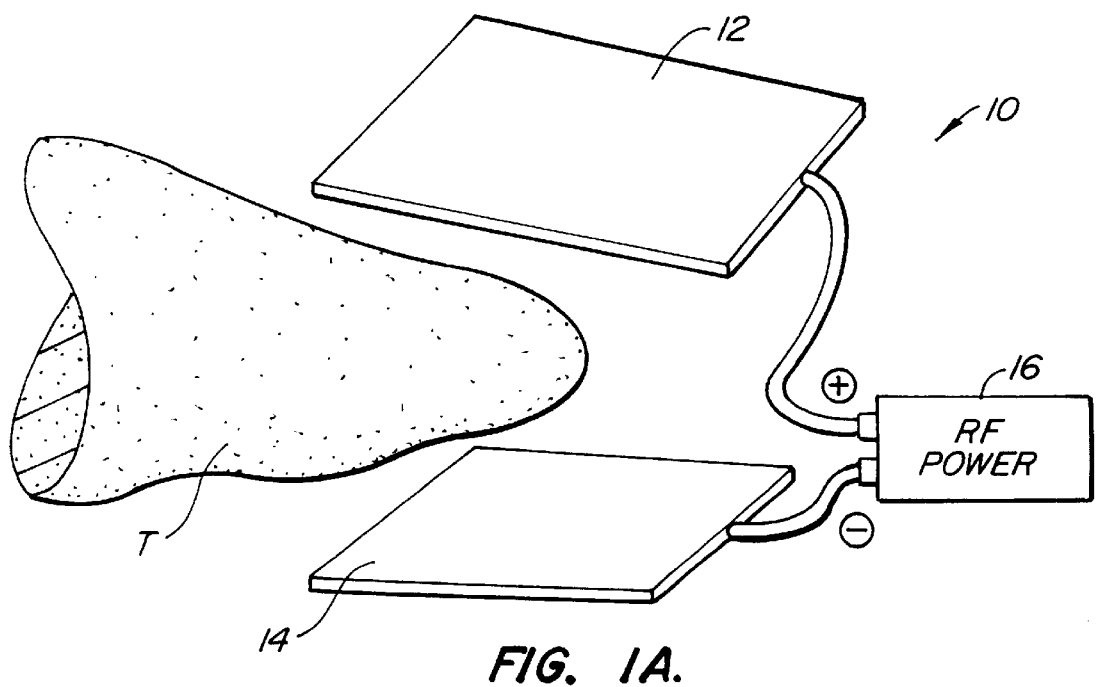
FIG. 1A is a conceptual illustration of the system and method of the present invention employing a pair of rigid, plate electrodes.

The methods, systems, and apparatus of the present invention will be useful for treating a variety of organs, portions of organs, or other solid tissue regions in a patient. The organ or other tissue mass will have spaced-apart tissue surfaces, usually opposed tissue surfaces, which are accessible to electrode structures and which permit the application of radio frequency power between said surfaces. The tissue surfaces may be readily accessible or may require pre-treatment in order to gain access, e.g. blunt dissection, resection of small tissues or blood vessels using conventional surgical techniques, or the like. Organs which may be treated by the present invention include the uterus, liver, prostate, kidney, bowel, pancreas, lung, breast, muscle, and the like.

The organs and other tissue will be treated with bipolar radio frequency power directed at target tissue regions which are defined by spaced-apart placement of the electrode structures. The radio frequency power may be supplied by conventional general purpose electrosurgical power supplies operated at any accepted frequency, typically in the ranges set forth above. Power supplies may employ conventional sinusoidal or non-sinusoidal wave forms and may operate with fixed or controlled power levels, where the voltage, current, or both may be selected. Suitable power supplies are available from commercial suppliers, such as Valleylab, Aspen, and Bovie. In some instances, it will be desirable to utilize impedance matching transformers between the power supply and the electrodes in order to enhance the efficiency of energy delivery.

The electrodes may be configured in any manner suitable for engaging a tissue surface. Thus, the electrodes can be rigid, flexible, elastic, inelastic (non-distensible), planar, non-planar, or the like, and may optionally employ tissue-penetrating elements to enhance electrical contact between the electrode structure and the tissue as well as to increase the electrode area. Preferred electrode configurations will either be conformable so that they can be engaged against and conform to widely differing tissue surfaces, or will be specifically configured to have a geometry intended to engage a particular organ or tissue geometry. In both instances, the electrode structures may further be provided with tissue-penetrating elements. Examples of each will be discussed hereinafter.

A preferred electrode configuration utilizes a metallized mesh which is both flexible and elastic. Such meshes are suitable for on retractable electrodes, such as retractable electrodes useful for minimally invasive procedures. The meshes may be suspended on or between more rigid frame members, where the frame members may be themselves expanded or contracted in order to deploy the mesh electrodes. Such meshes are also useful for fabricating elastic tubes or shells which may be placed over an organ or tissue mass like a "sock." In the case of such tubular electrodes, it will often be desirable to form two or more discrete electrode surfaces on a single mesh, where the electrode surfaces are isolated, usually by virtue of the material properties of the mesh itself, i.e. they are polymeric and non-conductive. The elastic meshes can be in the form of a braid or other woven structure, e.g. as described in U.S. Pat. Nos. 5,431, 676; 5,234,425; and 4,018,230, the full disclosures of which are incorporated herein by reference. The use of radially expansible braid structures is desirable since the diameter of the tissue-receiving lumen therein can be controlled by axial elongation. That is, the braid can be expanded by shortening its length and contracted by extending its length. All such mesh and braid structures can be metallized by conventional electroless plating techniques. Suitable for metals for plating include gold, silver, copper, stainless steel, and combinations and alloys thereof. Suitable elastomeric mesh materials include a wide variety of elastomers. Suitable braided mesh materials include nylon and other generally non-distensible polymers.

All types of electrode structures may be configured to have a conductive surface and a non-conductive surface. This is usually accomplished by leaving one surface as an "exposed" metallic face, while the other surface of the electrode is covered or insulated. In the case of rigid electrodes, the insulation can be laminated, coated, or otherwise applied directly to the opposed surface. In the case of flexible and elastic electrodes, it is necessary that the insulating layer also be flexible so that it can be expanded and contracted together with the electrode without loss or removal. In some cases, it will be desirable to employ a separate sheet of material which is expanded together with the electrode and which covers the face which is desired to be insulated.

Figure 1B:
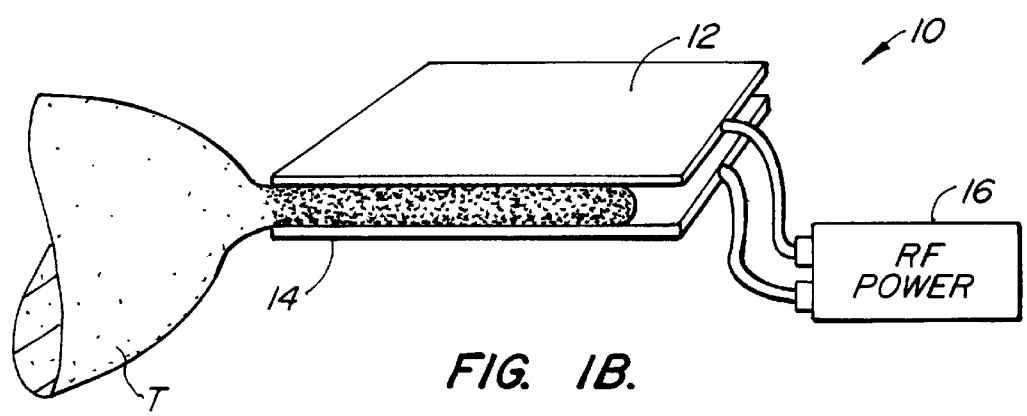
FIGS. 1B and 1C illustrate the use of the system of FIG. 1 in performing a tissue resection method according to the method of the present invention.
Figure 1C:
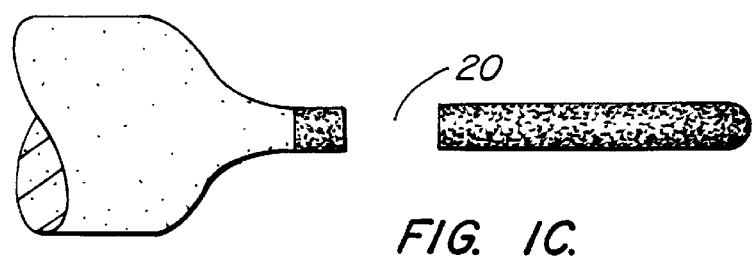

Referring now to FIGS. 1A–1C, a system 10 according to the present invention comprises a first electrode 12, a second electrode 14, and a radio frequency power supply 16. The first electrode is a rigid plate connected to one pole of the power supply 16 and the second electrode is a rigid plate connected to the opposite pole. The electrodes 12 and 14 can be engaged against a tissue mass T to engage opposed surfaces thereof, as illustrated in FIG. 1B. Radio frequency power is then applied to the tissue in order to completely necrose the mass of tissue which is captured between the electrodes 12 and 14. After the tissue is necrosed, it may be resected along a line 20 within the necrosed region of tissue, as illustrated in FIG. 1C. Advantageously, resection within the necrosed tissue minimizes bleeding and simplifies hemostasis.

Figure 1D:
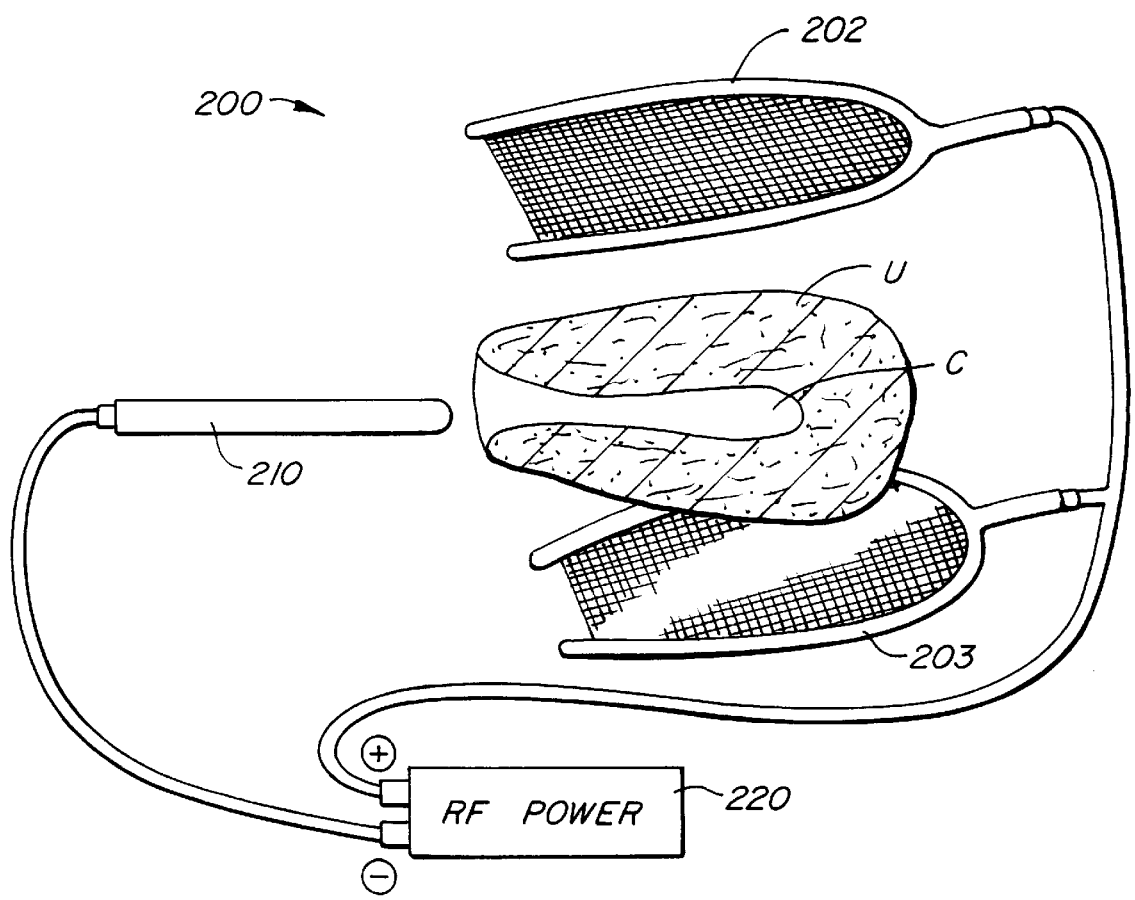
FIGS. 1D and 1E illustrate the system and method of the present invention employing a pair of conformable electrodes for applying high frequency energy in combination with a single electrode probe which is inserted into a natural body orifice.
Figure 1E:
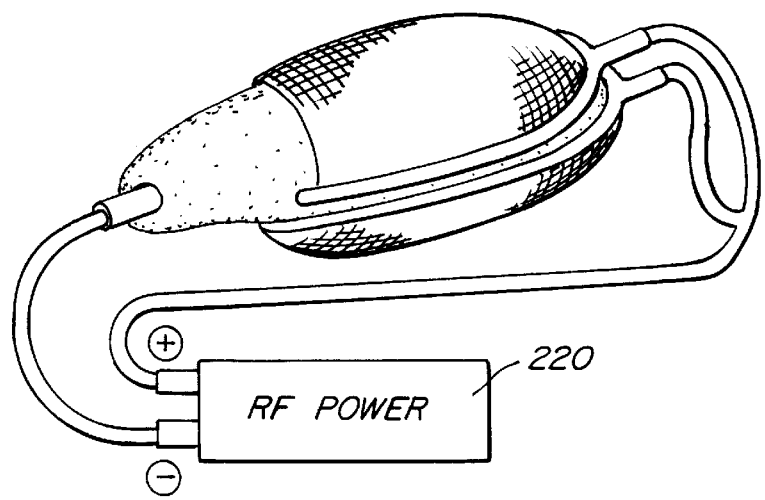

Referring now to FIGS. 1D and 1E, a system 200 according to the present invention comprises a first conformable electrode structure 202 and a second conformable electrode 203. The conformable electrode structures 202 and 203 comprise metallized elastomeric meshes, as generally described above. The system further comprises an electrode probe 210 which is suitable for introduction into a natural or other body lumen, illustrated as the uterine cavity C and a uterus U. The probe 210 may be rigid or flexible, and may have a geometry which is configured to conform to a target body lumen. Additionally, the probe may be configured for self-penetration into tissue to form a non-natural body lumen, e.g. it may have a sharpened distal tip.

For use in necrosing the tissue of uterus U, the conformable electrodes 202 and 203 may be placed over opposed exterior surfaces of the uterus. Rather than applying high frequency energy of opposite polarities, as generally described above, the electrodes 202 and 203 may be powered at a common polarity by power supply 220. The probe 210 may be inserted into the uterine cavity C and powered at the opposite polarity, as shown in FIG. 1E. In this way, the opposed tissue surfaces comprise the interior lining of the uterine cavity on the one hand and the exterior surface of the uterus on the other hand. In the case of the uterus, it will generally be desirable to necrose substantially the entire tissue mass, with the possible exception of the cervical neck. In the case of other body organs and tissue masses, however, it may be desirable to necrose only a portion of the tissue. The high frequency energy can be directed to limited portions of the tissue by choosing the configurations of the electrodes.

As illustrated thus far, each electrode structure has included only a single electrically active or conductive region. Electrode structures according to the present invention may optionally include a plurality of different electrically conductive regions, where the regions may be electrically isolated from each other or may be electrically coupled to each other. Single electrode structures may include three, four, five and as many as ten or more discrete electrically conductive regions thereon. Such electrically conductive regions will usually be defined by electrically insulating regions or structure therebetween. When it is desired that two or more of the electrically conductive regions be electrically coupled, small electrical connections can be provided to bridge the insulation between the regions. Usually, at least some of the isolated, electrically conductive regions on the electrode structures will be powered at opposite polarities, and in some instances the methods of the present invention can be performed using only a single electrode structure having multiple electrically conductive regions thereon. Alternatively, isolated, electrically conductive regions on a single electrode structure may be powered at the same polarity, where a primary purpose of the different regions is to control or configure the high energy electrical flux being delivered into the tissue mass. For example, it may be desirable to deliver high frequency electrical energy into spaced-apart regions of a tissue mass without necrosing other areas in between or adjacent to the region to be necrosed. In such cases, the electrode structures can be configured by appropriate placement of the electrically conductive regions.

Figure 1F:
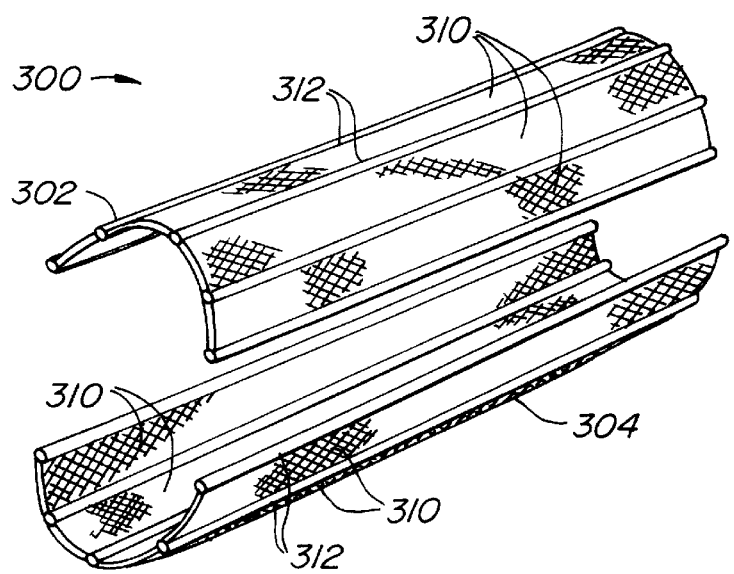
FIG. 1F illustrates an alternative electrode structure configuration where each electrode structure comprises a plurality of electrically isolated active surfaces.

Referring now to FIG. 1F, a system 300 comprises a pair of electrode structures 302 and 304. Each of the electrode structures 302 and 304 comprises five individual electrically conductive strips 310 which are electrically isolated form each other by intermediate rods 312 composed of an electrically insulating material. For example, the electrically conductive strips 310 may be fabricated from an electrically conductive mesh, while the rods 312 may be composed from a plastic or ceramic material having a high electrical impedance. The electrically conductive strips 310 may be selectively powered at different polarities in virtually any pattern. Often, it will be desirable to energize the strips so that adjacent strips have opposite polarities, as shown with a slightly modified electrode structure in FIG. 1G discussed below.

To this point in the description, the electrically conducted surfaces of the electrode structures have generally comprised rigid or conformable components having continuous surface geometries, i.e. surface geometries which are selected to create an uninterrupted interface with the tissue surface against which they are engaged. In some instances, it may be desirable to provide additional structure or components on the electrode structures in order to enhance or increase the effective electrical contact area between the electrode structure and the tissue surface. In particular, it will often be desirable to provide tissue-penetrating elements on the electrode structures to both enhance electrical contact (i.e. reduce electrical impedance between the electrode and the tissue) and, more importantly, to increase the total surface contact area between the electrode and the tissue. The tissue-penetrating elements may be needles, pins, protrusions, channels, or the like, but will usually be pins having sharpened distal tips so that they can penetrate through the tissue surface and into the underlying tissue mass. The pins may have depths in the rage from 1 mm to 5 cm, usually being from 3 mm to 1 cm. The diameters of the pins may be from 0.1 mm to 5 mm, usually being from 0.5 mm to 3 mm. Usually, the pins will be evenly distributed over the tissue-contact area of an electrode structure, with a pin density in the range from 0.1 pin/cm$^2$ to 10 pin/cm$^2$, usually from 0.5 pin/cm$^2$ to 5 pin/cm$^2$. Usually, the pins or other tissue-penetrating elements will be provided in addition to an electrically conductive conformable or rigid electrode surface, but in some instances the pins may provide the total electrically conductive or active area of an electrode structure.

Figure 1G:
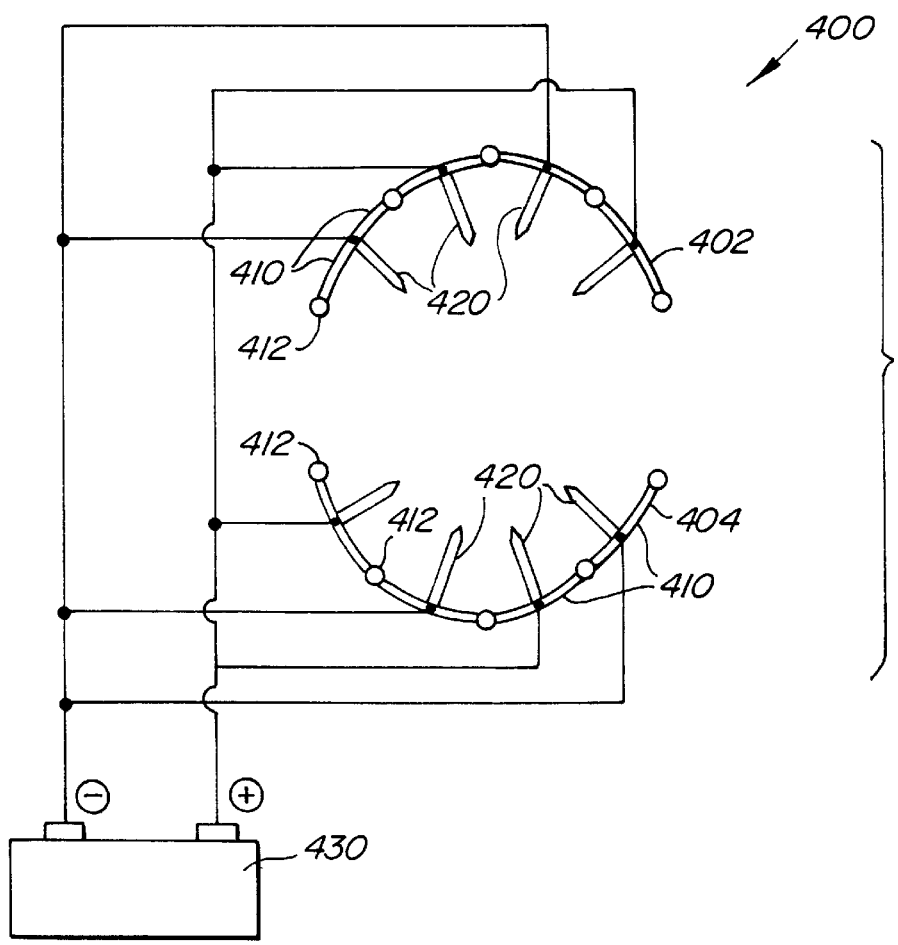
FIG. 1G illustrates a pair of electrode structures similar to those illustrated in FIG. 1F and further comprising a plurality of tissue-penetrating elements on each of the electrically active surfaces.

Referring now to FIG. 1G, a system 400 comprises a pair of electrode structures 402 and 404. The electrode structures 402 and 404 are generally the same as electrode structures 302 and 304 in system 300 of FIG. 1F and include electrically conductive strips 410 separated by insulating rods 412. In addition, however, tissue-penetrating pins 420 are disposed along each of the electrically conductive strips 410. While only one pin 420 is visible on each of the strips 410, it will be appreciated that a plurality of pins are disposed along the length of each strip. The electrode structures 402 and 404 are shown in a generally curved configuration so that they may be placed over a tubular body structure or tissue mass. It will be appreciated, however, that the strips 410 may be formed from conformable meshes which would permit the electrode structures to be flattened out or assume a wide variety of other configurations. Additionally, the insulating structures 412 may also be formed from a flexible or conformable material, permitting further reconfiguration of the electrode structures 402 and 404.

The electrically conductive strips 410 may be energized in an alternating polarity configuration, as illustrated in FIG. 1G. Most simply, adjacent strips will be connected to opposite polls on a single power supply 430. It would be a simple matter, however, to rearrange the electrical connections to power the strips in virtually any pattern. Moreover, it would also be possible to electrically isolate different axial regions of each strip 410 in order to permit powering those regions at different polarities.

Figure 1H:
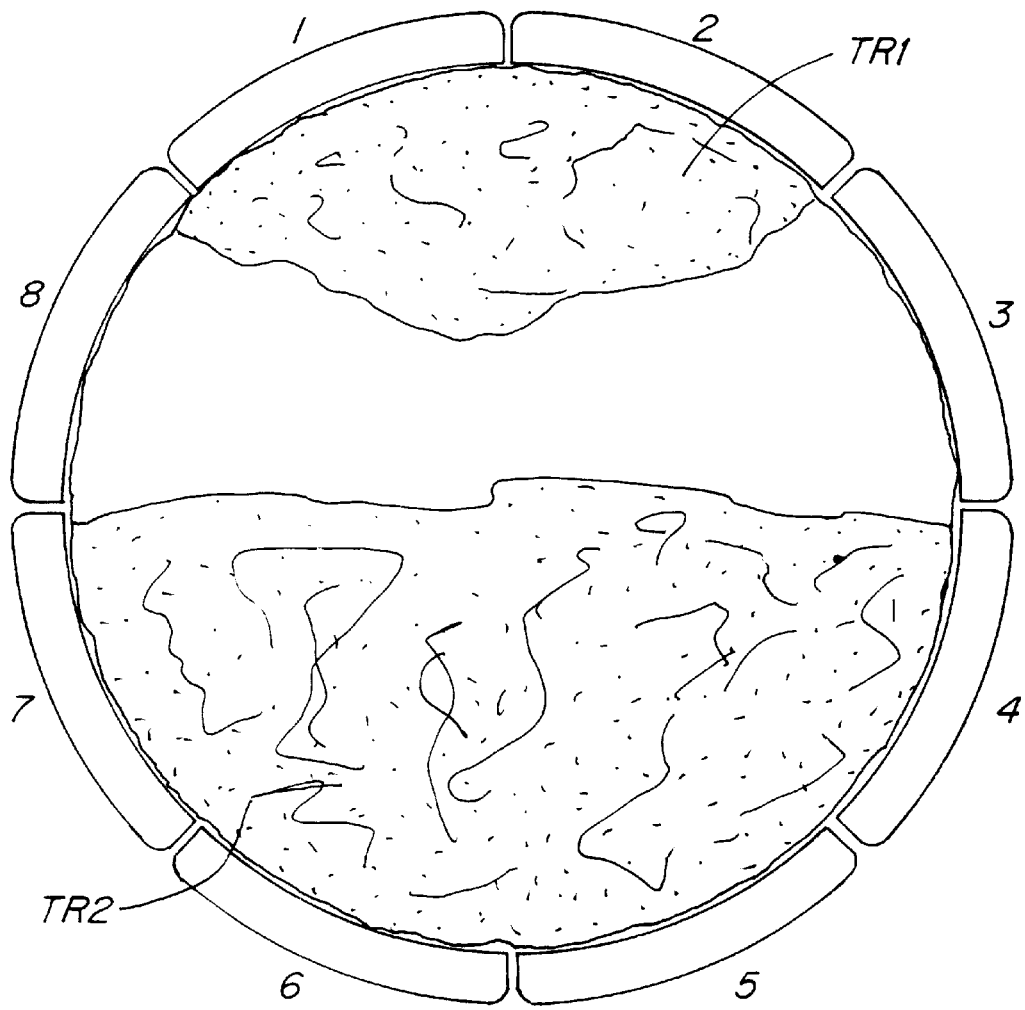
FIG. 1H illustrates different tissue necrosis patterns that can be achieved by selective energization of the electrode structures of FIGS. 1F and 1G.

Using either system 300 or system 400, a variety of different tissue necrosis patterns can be achieved by selective energization of different ones of the electrode surfaces or regions. As schematically illustrated in FIG. 1H, by selectively energizing two adjacent electrode surfaces (nos. 1 and 2) in a bipolar fashion, while leaving all other surface non-energized, a limited tissue region TR1 will be necrosed. In contrast, by energizing electrode surface nos. 4, 5, 6, and 7, a much larger region will be necrosed. Slightly different patterns will be achieved depending on the precise pattern of electrode surface polarity. As shown in FIG. 1H, the electrode surfaces will be energized in an alternating pattern of polarity (+, −, +, −) to produce tissue necrosis pattern TR2. Patterns of (+, +, −, −); (+, −, −, +); (−, +, +, −) etc., could also be used to produce somewhat different patterns of necrosed tissue.

Figure 2:
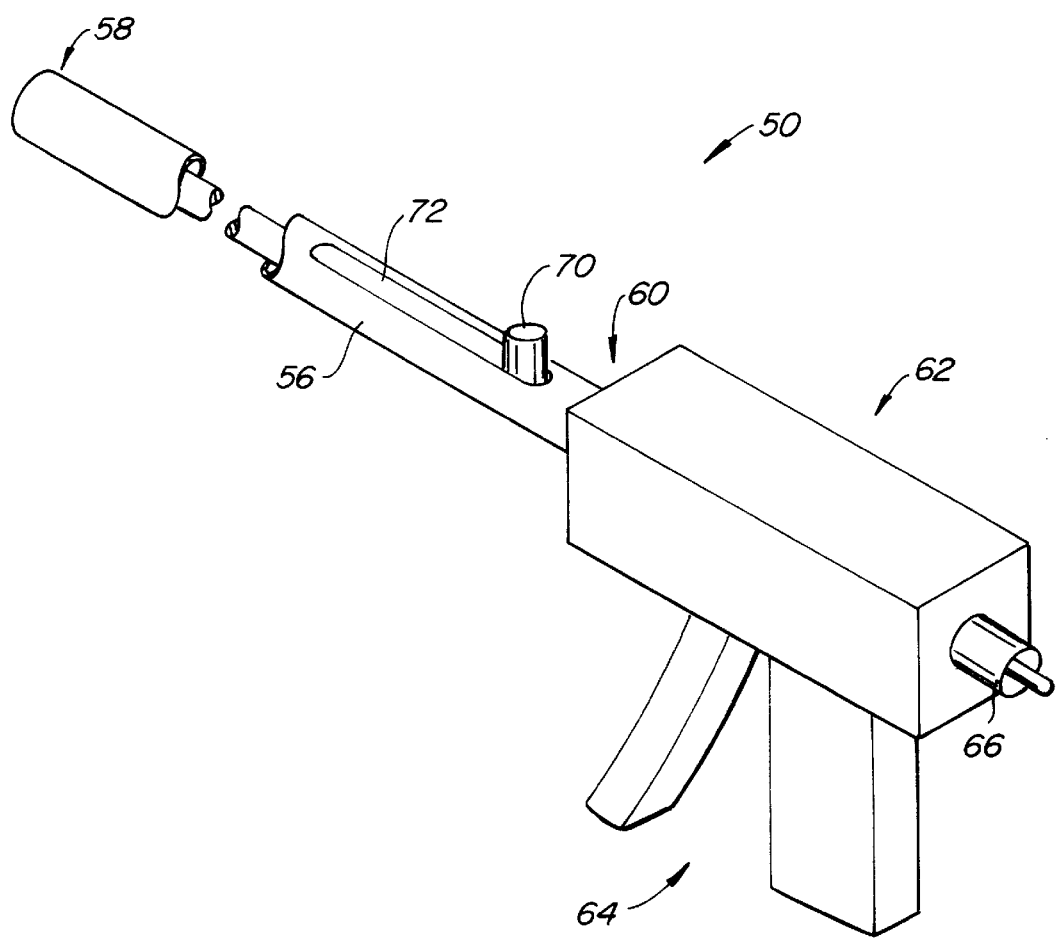
FIG. 2 illustrates an electrosurgical probe configured for minimally invasive surgical use.
Figure 3:
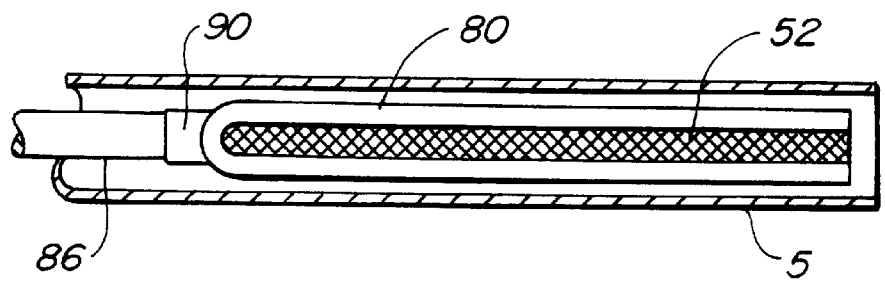
FIGS. 3 and 4 illustrate the electrodes and electrode deployment of the electrosurgical probe of FIG. 2.
Figure 4:
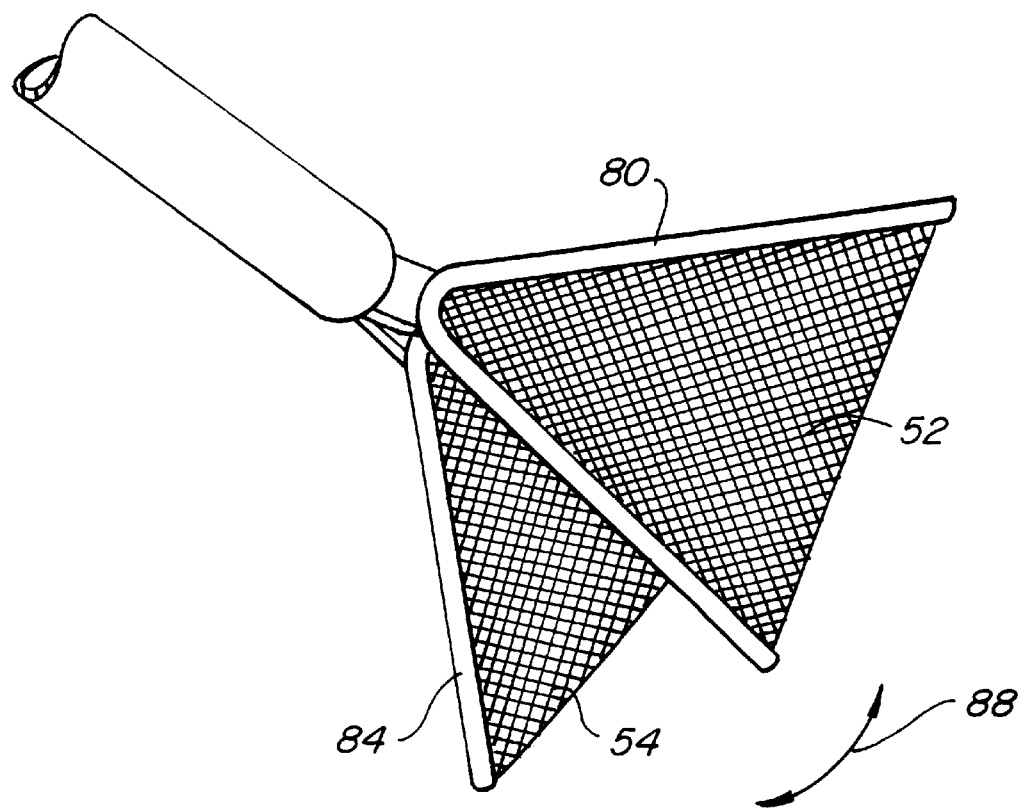

Referring now to FIGS. 2–4, an electrosurgical probe 50 intended for deploying opposed, wire mesh electrodes 52 and 54 (FIG. 4) will be described. The electrosurgical probe 50 includes a shaft 56 having a distal end 58 and a proximal end 60. The shaft is typically a cylinder sized for introduction through a conventional cannula of the type used in minimally invasive surgery. Thus, the shaft will typically have a diameter in the range from 5 mm to 15 mm, usually being nominally 5 mm, 10 mm, or 12 mm, to be consistent with conventional cannulas. The length of the shaft will typically be in the range from 10 cm to 30 cm, with the particular range depending on the intended procedure.

The electrosurgical probe 50 will include a handle assembly 62 attached to the proximal end 60 of the shaft 56. The handle will include a lever assembly 64 which will be connected to actuate the electrodes 52 and 54 after they are forwardly deployed, as described hereinafter. The handle also includes a coaxial connector 66 for connecting the electrodes 53 and 54 to a conventional electrosurgical power supply. The electrosurgical probe 50 further comprises a tab 70 and slot 72 formed in the shaft 56 to permit advancement and retraction of the electrodes 52 and 54.

The electrodes 52 and 54 are secured between the legs of resilient fork assemblies 80 and 84, respectively. The resilient fork assemblies 80 and 84 permit the electrodes 52 and 54 to be collapsed when they are retracted within the shaft 56, as illustrated in FIG. 3. When forwardly deployed from the shaft 56, the electrodes expand into their open configurations, as shown in FIG. 4. The electrodes 52 and 54 may be opened and closed in a jaw-like manner in the direction of arrow 88, as shown in FIG. 4. The handle assembly 64 will be coupled to the electrodes through a conventional jaw mechanism 90 located at the end of rod 86 which carries the electrodes 52 and 54 via the assemblies 80 and 84. The rod 86 may be advanced and retracted using the tab 70 which is attached to a proximal thereof.

Figure 5:
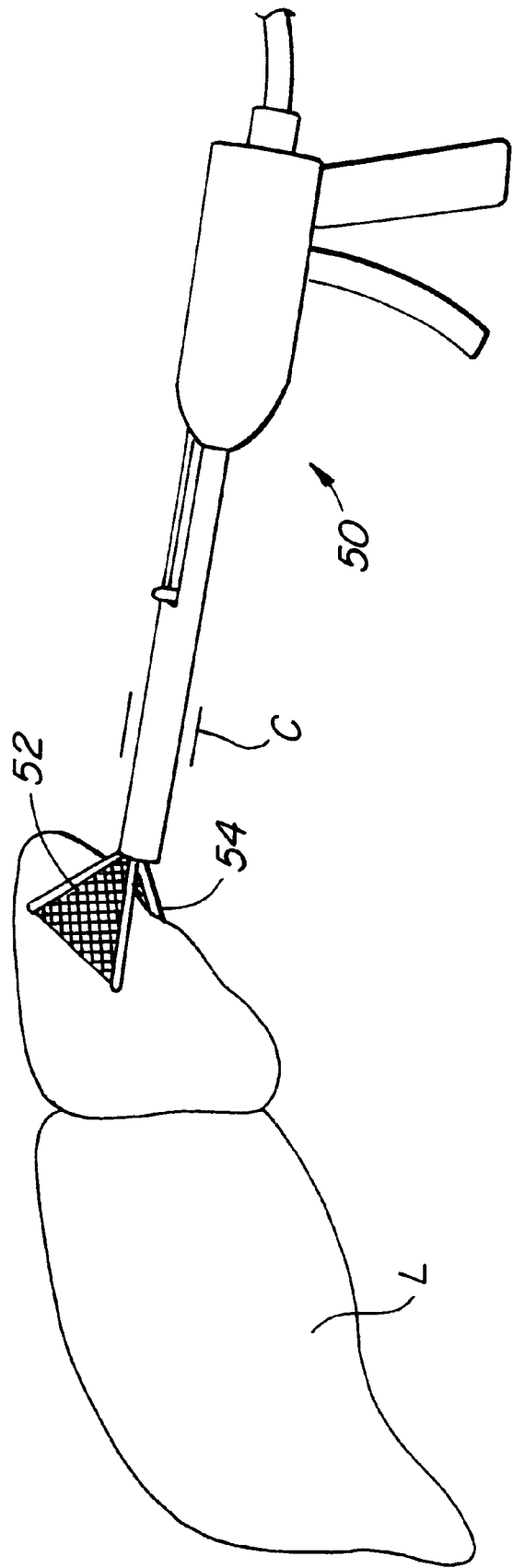
FIG. 5 illustrates use of the electrosurgical probe of FIG. 2 in necrosing a liver section according to the methods of the present invention.

The electrosurgical probe 50 may be employed to necrose and resect a portion of liver L, as illustrated in FIG. 5. For example, the probe may be introduced through a cannula C, and the electrodes 52 and 54 advanced and opened so that they can capture a portion of the liver L which is to be removed. After the electrodes 52 and 54 are closed against opposed surfaces of the liver, the radio frequency energy may be applied as described above. After the tissue is fully necrosed, it may be resected along any line within the necrosed tissue mass. Optionally, the electrosurgical probe 50 may be used to necrose a series of tissue masses adjacent each other in order to necrose and resect a larger tissue mass than would be possible using only a single application of radio frequency energy.

Figure 6:
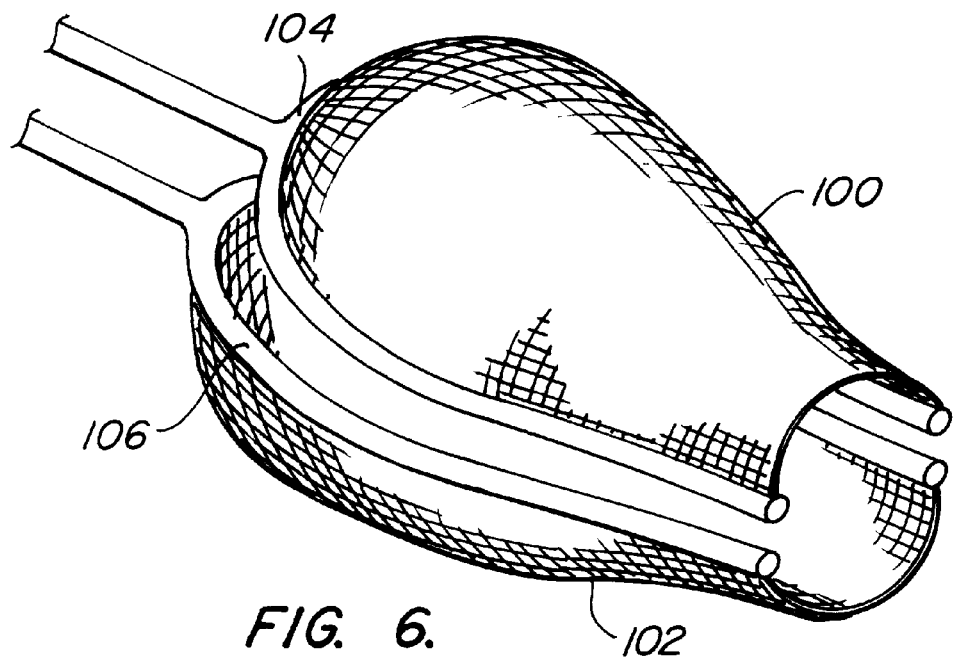
FIG. 6 illustrates a preferred electrode configuration for use in necrosis and removal of a uterus according to the methods of the present invention.

Referring now to FIG. 6, a pair of electrodes 100 and 110 which are configured especially for engaging the exterior surface of a uterus is illustrated. The electrodes comprise frame members 104 and 106 which hold metallized mesh electrode portions which are generally shaped to conform to the exterior surface of the uterus. Optionally, the meshes may be elastic in order to tightly conform to the outer tissue surface.

Figure 7:
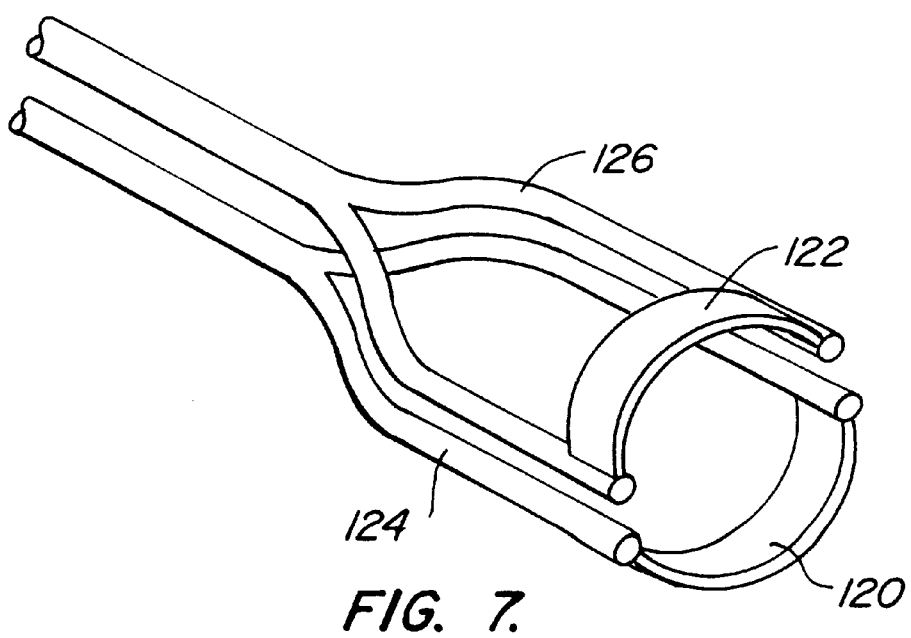
FIG. 7 illustrates an alter native preferred configuration for an electrosurgical probe for removing a uterus according to the methods of the present invention.

An alternative electrode configuration intended to engage only the cervical neck of a uterus is illustrated in FIG. 7. The electrode assembly comprises first and second half-ring electrodes 120 and 122. These electrodes may be rigid, flexible, or elastic. Typically, they will be flexible (but not necessarily elastic) so that they can conform over the neck of the cervix, as described below. The electrodes 120 and 122 are suspended at the end of a pair of devises 124 and 126, respectively.

Figure 9:
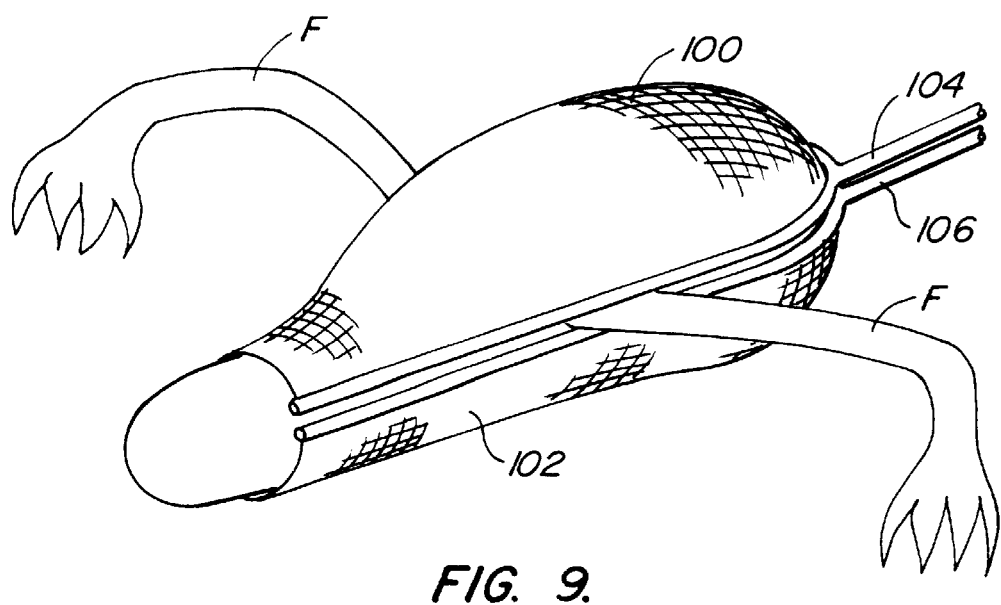
Figure 10:
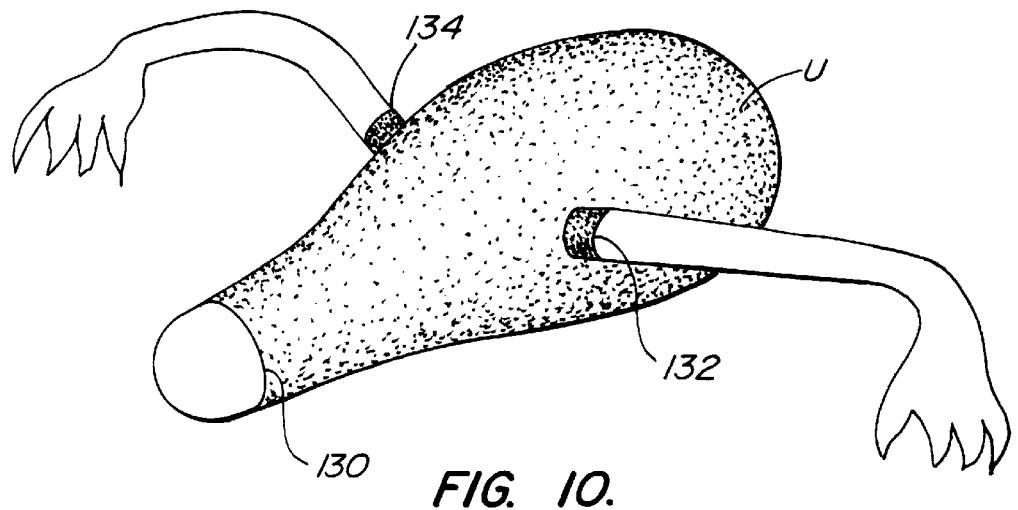
Figure 11:
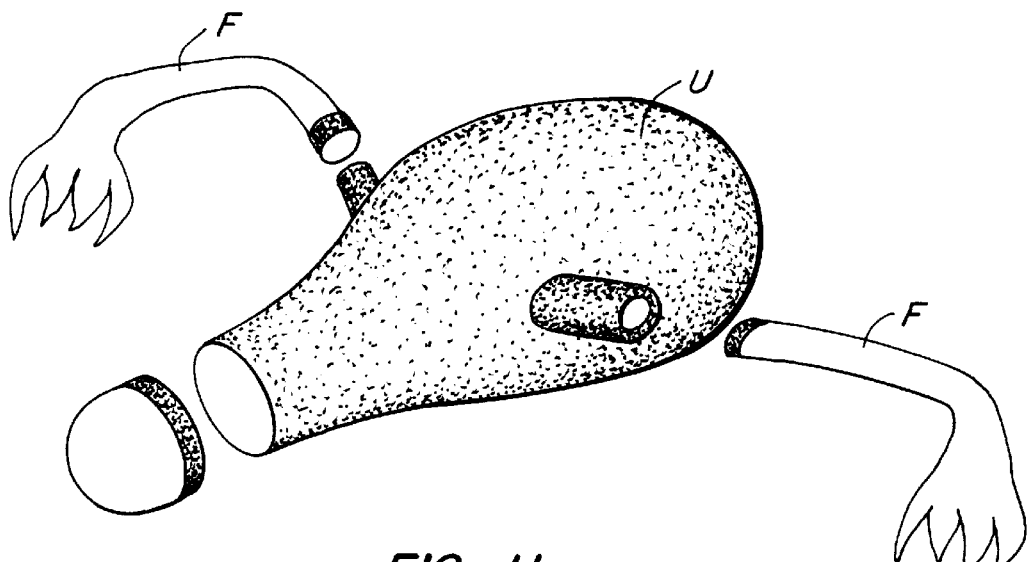
Figure 12:
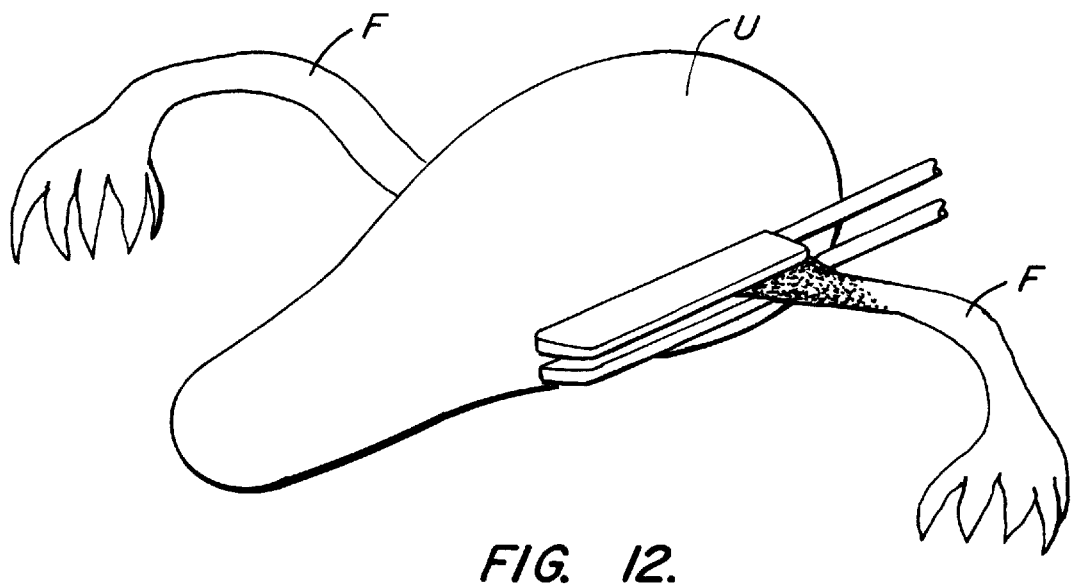
FIGS. 12–15 illustrate use of the probe of FIG. 7 for removing a uterus according to the methods of the present invention.

The electrodes 100 and 102 (FIG. 6) may be used to necrose and resect a uterus U, as illustrated in FIGS. 8–11. The uterus comprises a main body having fallopian tubes F extending from each side. In addition to the fallopian tubes, several large blood vessels extend generally from the midline of the uterus. The electrodes 100 and 102 may be placed over the anterior and posterior surfaces of the uterus with the fallopian tubes F remaining attached and extending outwardly from between the frame members 104 and 106, as illustrated in FIG. 9. Radio frequency power may then be applied to the uterus, typically at a power level in the range from 1 W/cm$^2$ to 5 W/cm$^2$ for a time in the range from 1 min. to 20 min., until the body of the uterus is substantially completely necrosed, as illustrated in FIG. 10. Because of the geometry of the electrodes 100 and 102, the necrosed body of the uterus will terminate along a line 130 generally at the cervical end of the uterus, as well as along lines 132 and 134 adjacent the fallopian tubes F. The uterus may then be resected along lines within the necrosed tissue region but adjacent the cervix and fallopian tubes, as generally shown in FIG. 11. Resection within the necrosed regions of the uterus substantially minimizes bleeding and facilitates hemostasis. The uterus may then be removed, either intact in the case of open surgical procedures. In the case of minimally invasive procedures, the uterus may optionally be morcellated (comminuted into small pieces) prior to removal.

Figure 7A:
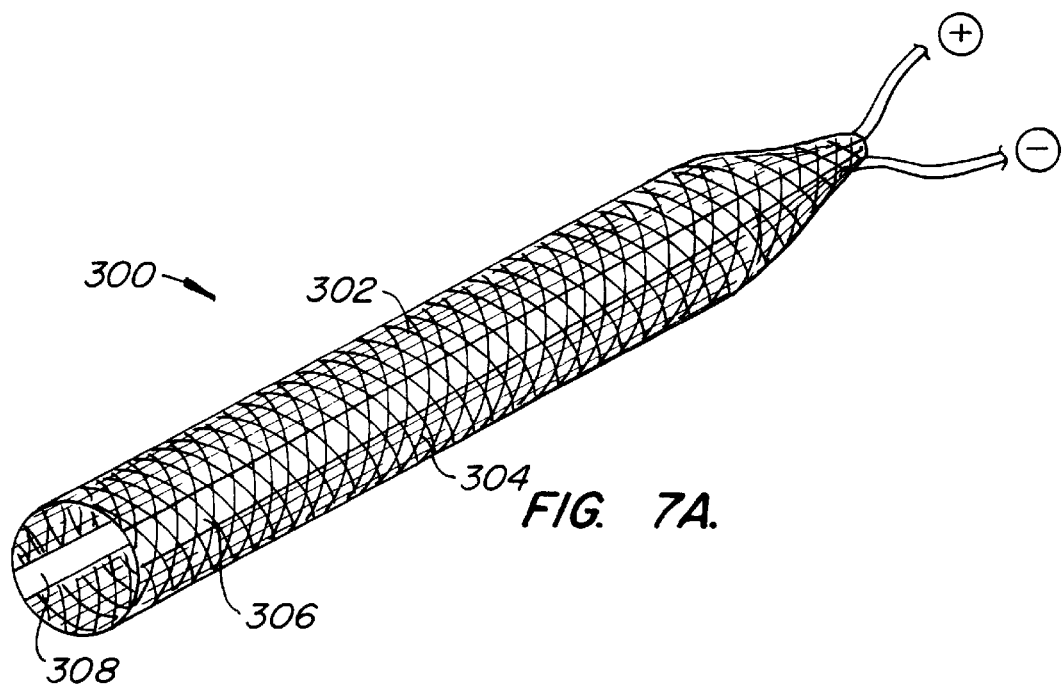
FIGS. 7A and 7B illustrate an electrosurgical probe comprising a single conformable support structure, with the support structure in a collapsed or retracted configuration in FIG. 7A and in a radially expanded configuration in FIG. 7B.
Figure 7B:
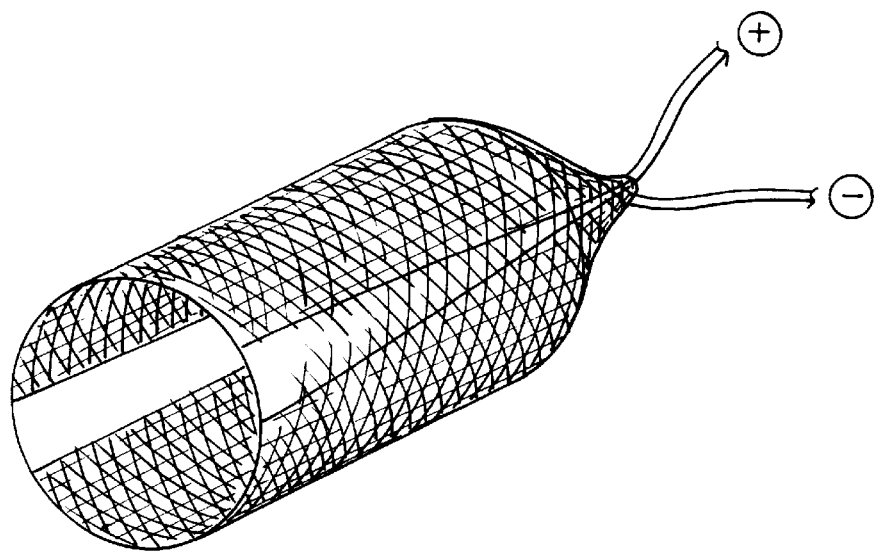

Referring now to FIGS. 7A and 7B, an alternative structure 300 for supporting a pair of opposed electrodes will be described. The structure comprises a single conformable support structure, shown as a tubular braided mesh. Such meshes are well described in the medical patent literature, e.g. in the patents which were previously incorporated herein by reference. The tubular braided mesh structure is well known, and one or more electrode surfaces may be formed on the support structure by electroless plating techniques. In the illustrated embodiment 300, opposed, arcuate electrode surfaces 302 and 304 are formed on opposite sides of tubular braided support and separated by non-metallized strips 306 and 308. Generally, the non-metallized strips will be sufficient to isolate the electrodes 302 and 304, but placement of additional insulation may also be performed. The structure 300 is shown in a radially collapsed configuration in FIG. 7A. The structure may be radially expanded by axial shortening, as shown in FIG. 7B. The expanded structure may then be conformed over a tissue surface by axial elongation.

Figure 7C:
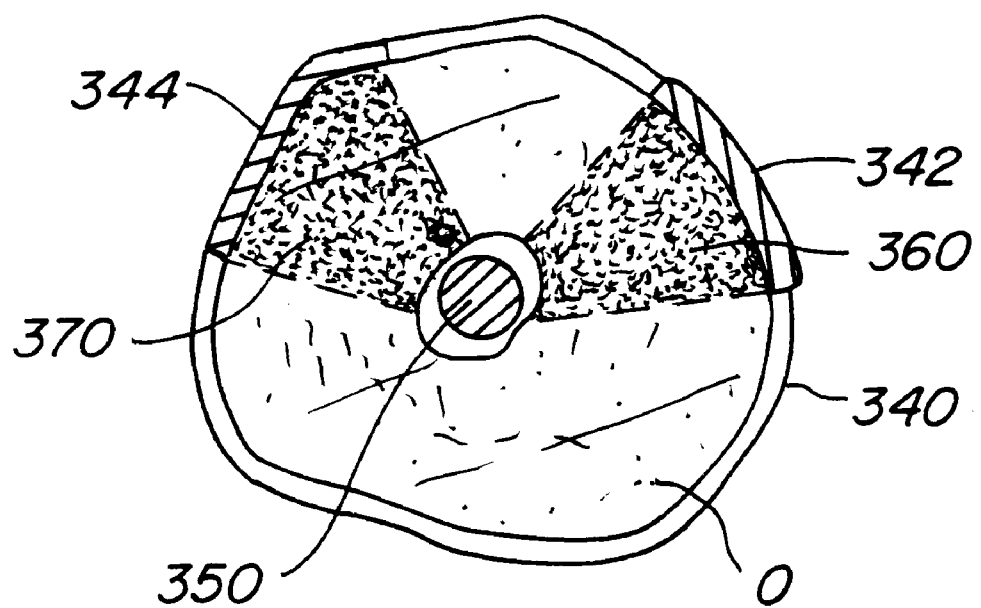
FIG. 7C illustrates use of an electrosurgical probe comprising a conformable support structure having non-symmetrically placed electrode surfaces in combination with a separate electrosurgical probe.
Figure 8:
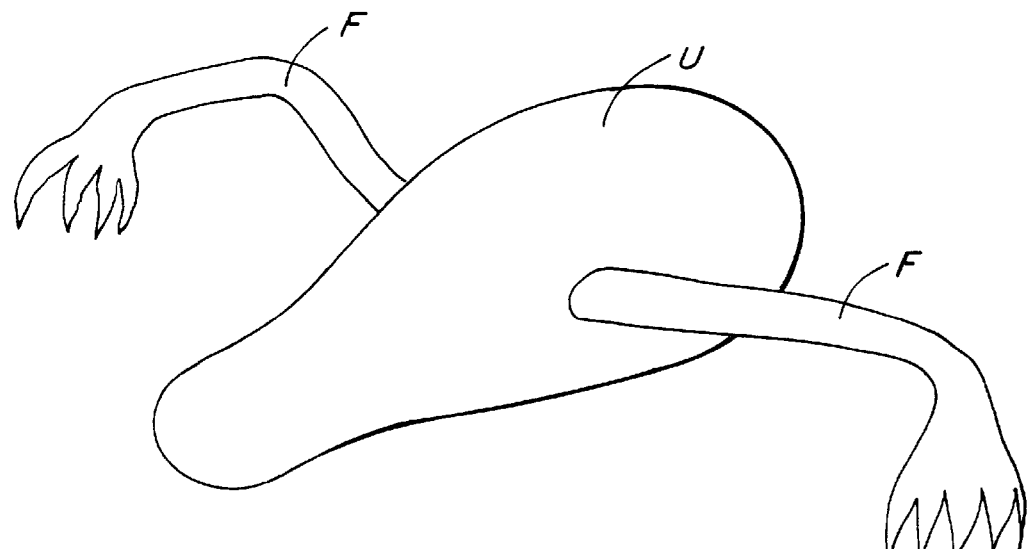
FIGS. 8–11 illustrate use of the probe of FIG. 6 for removing a uterus according to the methods of the present invention.

Referring now to FIG. 7C, a conformable tubular support structure 340 may have two or more non-symmetrically placed electrode surfaces 342 and 344 formed thereon. By placing the structure 340 over an organ O and inserting a separate electrosurgical probe 350 into a natural or created lumen within the organ, select portions of the tissue mass may be necrosed, as shown by shaded areas 360 and 370. Optionally, an electrically conductive fluid may be introduced into the lumen to enhance electrical coupling of the probe electrode to the tissue.

Figure 13:
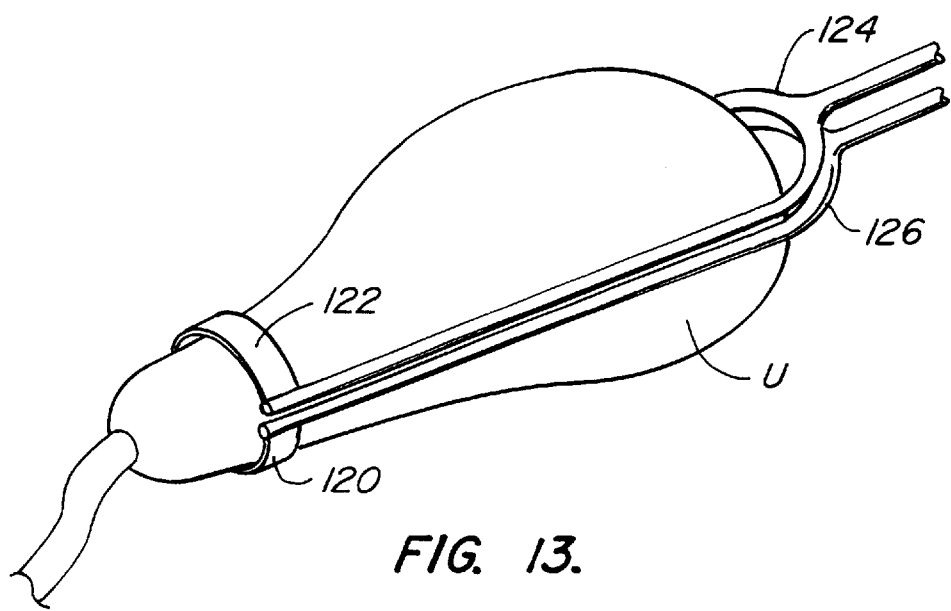
Figure 14:
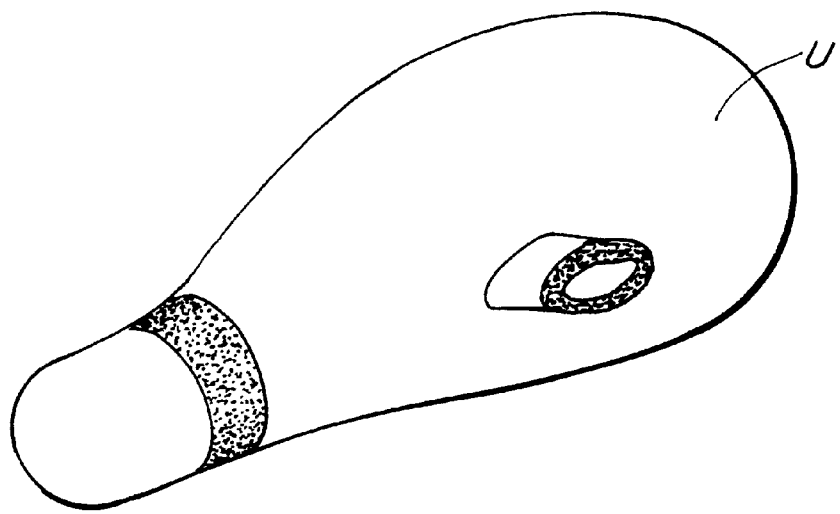
Figure 15:
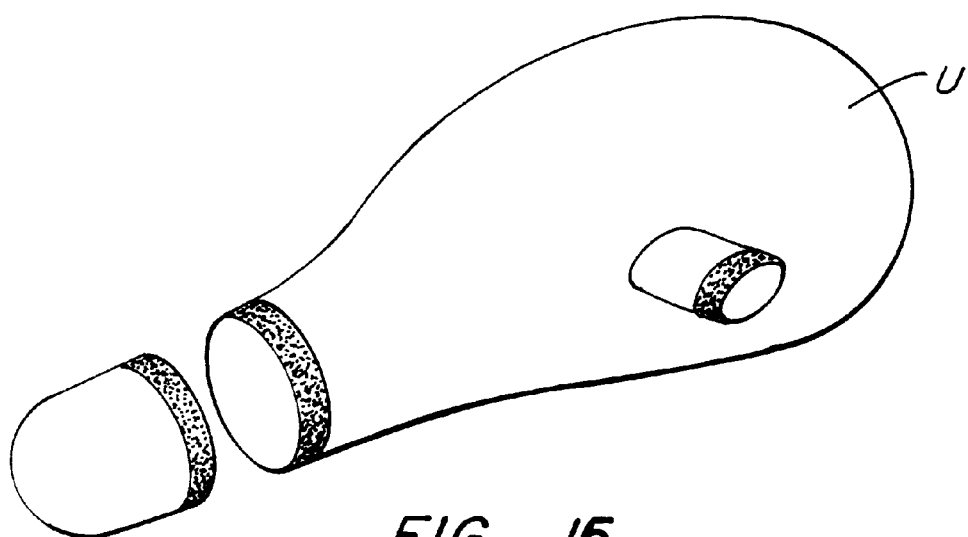

Use of the electrodes 120 and 122 illustrated in FIG. 7 for removing the uterus U in a two-step procedure is illustrated in FIGS. 12–15. First, the fallopian tubes F may be necrosed using opposed spatula electrodes or electrosurgical blades. When spatula electrodes are used, the necrosed regions may then be resected, generally in accordance with the methods of the present invention. The fallopian tubes and other blood vessels, however, may also be resected by conventional techniques. The electrodes 120 and 122 are used to facilitate resection of the cervical end of the uterus. The electrodes 120 and 122 are placed around the neck of the cervix, as shown in FIG. 13, and radio frequency power applied to necrose the tissue therebetween. The resulting region of necrosed tissue, as shown in FIG. 14, may then be resected in order to permit removal of the uterus U.

Optionally, an electrode may also be placed within the cervical opening as illustrated in FIG. 13. The electrode may be a conventional rod-type electrode and may act as the common or return electrode in the electrosurgical treatment. When such a cervical electrode is used, the electrodes 120 and 122 may be operated as a single pole of the bipolar treatment, where the cervical electrode is the opposite pole.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for resecting tissue in a patient, said method comprising:

engaging a first electrode structure and a second electrode structure against opposed surfaces of a tissue mass prior to resecting the tissue mass from the patient, wherein each electrode has a surface area of at least 1 $cm^2$;

applying high frequency power through said electrodes to said tissue mass, wherein said power is applied for a time and in amount sufficient to necrose said tissue mass between said electrode structures;

stopping the high frequency power application; and resecting the tissue within the necrosed tissue mass after the tissue has been necrosed and the application of high frequency power stopped.

2. A method as in claim 1, wherein the engaging step comprises engaging a first electrode structure which spans an area of at least 2 $cm^2$ against a first tissue surface and engaging a second electrode structure which spans an area of at least 2 $cm^2$ against a second tissue surface.

3. A method as in claim 2, wherein the engaging step comprises contacting at least one of the tissue surfaces with a flat or conformable electrode surface in a surface-to-surface manner.

4. A method as in claim 2, wherein the engaging step comprises penetrating a plurality of tissue penetrating elements into at least one of the tissue surfaces.

5. A method as in claim 2, wherein the engaging step further comprises expanding at least one of the first and second electrode structures from a retracted configuration to an expanded configuration prior to said electrode structure against the tissue surface.

6. A method as in claim 5, wherein the at least one electrode structure comprises an elastic or expansible braid or woven support.

7. A method as in claim 5, wherein the electrode structure comprises non-distensible surface.

8. A method as in claim 1, further comprising introducing the first and second electrode structures through a percutaneous access port prior to engaging said electrode structures against the tissue mass surfaces.

9. A method as in claim 8, wherein said electrode surfaces are introduced in a retracted configuration through the access port and are thereafter expanded prior to the engaging step.

10. A method as in claim 1, wherein the tissue mass is a body organ.

11. A method as in claim 10, wherein the opposed surfaces are on the exterior of the body organ.

12. A method as in claim 10, wherein one of the tissue surfaces is defined by a natural lumen within the organ and the other surface is on the exterior of the body organ.

13. A method as in claim 12, further comprising introducing an electrically conductive fluid into the lumen to enhance electrical coupling of an electrode structure in the lumen to the tissue surface.

14. A method as in claim 10, further comprising dissecting an exterior surface of the body organ away from adjacent tissue prior to the engaging step structure.

15. A method as in claim 10, further comprising creating an incision in the tissue mass, wherein the incision exposes at least one tissue surface for engagement with an electrode structure.

16. A method as in claim 1, wherein the applying step comprises applying radio frequency current at a frequency in the range from 100 kHz to 10 MHz and a power in the range from 1 $W/cm^2$ to 10 $W/cm^2$.

17. A method as in claim 16, wherein the applying step comprises heating the tissue between said opposed electrodes to a temperature above 60° C.

18. A method as in claim 1, wherein the applying step defines a volume of necrosed tissue between said necrosed electrodes having a boundary between the necrosed tissue and adjacent viable tissue.

19. A method as in claim 18, wherein the resecting step comprises morcellating at least a portion of the tissue volume but not the adjacent viable tissue.

20. A method as in claim 1, wherein the engaging step comprises engaging a pair of semi-circular electrode structures against opposed sides of a tubular tissue mass.

21. A method as in claim 20, wherein the semi-circular electrodes are engaged to circumscribe the tubular tissue mass.

22. A method as in claim 20, where in the applying step creates a planar, disk-like region of necrosed tissue within the tubular body mass.

23. A method as in claim 22, wherein the resecting step comprises cutting along a plane within said disk-like region of necrosed tissue.

24. A method as in claim 1, further comprising removing the resected tissue from the patient.

25. A method as in claim 24, wherein the removing step comprises morcellating the tissue.

26. A method as in claim 1, wherein the engaging step comprises engaging a first electrode surface which spans an area of at least 5 $cm^2$ against a first tissue surface and engaging a second electrode surface which spans an area of at least 5 $cm^2$ against a second tissue surface.

27. A method as in claim 1, wherein the engaging step comprises engaging a first electrode surface which spans an area of at least 10 $cm^2$ against a first tissue surface and engaging a second electrode surface which spans an area of at least 10 $cm^2$ against a second tissue surface.

28. A method as in claim 1, wherein the engaging step comprises engaging a first electrode surface which spans an area of at least 50 $cm^2$ against a first tissue surface and engaging a second electrode surface which spans an area of at least 50 $cm^2$ against a second tissue surface.

* * * * *